United States Patent [19]

Wirtz

[11] Patent Number: 5,302,981
[45] Date of Patent: Apr. 12, 1994

[54] METHOD AND APPARATUS TO CORRECT VERTICAL AND LATERAL DOUBLE VISION

[76] Inventor: Paul C. Wirtz, 20 King Rd., Lebanon, N.J. 08833

[21] Appl. No.: 964,712

[22] Filed: Oct. 22, 1992

[51] Int. Cl.$^5$ ............................. A61B 3/00; A61B 3/02
[52] U.S. Cl. .................................... 351/246; 351/222; 351/224; 351/225
[58] Field of Search ............... 351/224, 225, 226, 246, 351/201, 202, 222

[56] References Cited

U.S. PATENT DOCUMENTS

| | | |
|---|---|---|
| 439,130 | 10/1890 | Edmunds . |
| 1,091,701 | 3/1914 | Pixley . |
| 2,118,132 | 5/1938 | Ames, Jr. et al. . |
| 2,442,849 | 6/1948 | Glazer . |
| 4,427,272 | 1/1984 | Gernet . |
| 4,854,694 | 8/1989 | Hirano et al. .................... 351/224 |
| 5,094,521 | 3/1992 | Jolson et al. ...................... 351/246 |

OTHER PUBLICATIONS

Irvine, "Measuring Scotomas with the Prism-Displacement Test", Amer. J. of Ophthalmology vol. 61, No. 5, May 1966, pp. 1177/237-1187/247.
Sulman, "The Strabismometer and Its Function", Optometric Weekly vol. 48 No. 37, Sep. 12, 1957, pp. 1747-1750 and 1773.
Glasser, Emanuel S., O. D., *Considerations When Prescribing Large Degrees of Prism,* Optical Journal-Rieview, Jan. 1, 1965, pp. 23-24.

Primary Examiner—Loha Ben
Assistant Examiner—Michael A. Papalas
Attorney, Agent, or Firm—Watov & Kipnes

[57] ABSTRACT

A method for prescribing a prism factor for eyeglasses for substantially correcting vertical and/or horizontal diplopia or double vision problems, which includes having a patient positioned for gazing at a target image while holding their head in a substantially fixed position, and then closing their affected eye for a period of time, whereafter they are instructed to open the affected eye and immediately report upon where a double image occurs upon a measurement grid associated with the target image continuing to be observed by their other eye, for permitting a prism factor to be prescribed relative to the measured distance between the target and double image created by the defective eye. The minimum necessary prism factor for correcting the vision of the defective eye to provide for merger of the target image observed by the other eye with that of the defective eye upon opening, permits maximization of the involvement of the eye muscles of the defective eye in combination with the prescribed prism for substantially extending the range of correction of the diplopia problem.

15 Claims, 3 Drawing Sheets

METHOD AND APPARATUS TO CORRECT VERTICAL AND LATERAL DOUBLE VISION

FIELD OF THE INVENTION

The field of the present invention relates generally to eyeglasses and apparatus for assisting in prescribing eyeglasses, and more particularly relates to methods and apparatus for relieving double vision problems.

BACKGROUND OF THE INVENTION

Many people experience eye defects causing vertical double vision problems in some cases, and lateral double vision problems in other cases. Such problems can be caused by injury to the retina, cataract operations, and so forth.

There have been many attempts in the prior art to provide apparatus and methods for prescribing eyeglasses to correct double vision problems. It is known to use prisms in eyeglasses to correct double vision problems. A brief discussion of the teachings of known references follows below.

Edmunds, U.S. Pat. No. 439,130, teaches the use of prisms in eyeglasses for providing a magnification to the user in a binocular manner. Note beginning at line 38, it is recognized that convex lenses used by normal sighted persons may cause double vision. It is indicated that by using prism-shaped lenticular convex surfaces, correction of the double vision problem is obtained.

Pixley, U.S. Pat. No. 1,091,701 teaches an instrument for detecting heterophoria. The instrument taught is used to test the muscles of the eyes for determining the appropriate lenses for correcting double vision or diplopia. The instrument permits the muscle error to be determined in the affected eye, for prescribing an appropriate prism.

Ames, Jr., et al., U.S. Pat. No. 2,118,132 teaches the use of eyeglasses having multiple lenses for each eye, with the lenses being prismatic in their configuration, for correcting a defect in the eye known as "aniseikonia", that causes blurring of images due to differences in the size and/or shape of the images in binocular vision. It is indicated that when prisms are used to correct a condition known as "phoria", the prisms themselves may cause the user to have distortional aniseikonia.

Glazer, U.S. Pat. No. 2,442,849 teaches the use of prismatic lenses and eyeglasses for correcting double vision, particularly when users move their line of sight away from a limited central zone. It is recognized that prismatic lenses used for correcting one defect, may create other problems such as causing double vision, and eye strain.

Gernet, U.S. Pat. No. 4,427,272 shows an eyeglass lens provided with a prismatic shape, but of stepped thickness, for providing progressive magnification. The lens is associated with aniseikonia eyeglass lenses. This type of lens is used for correcting defects in binocular vision in which the two retinal images of an object differ in size.

An article by Emanuel S. Glasser, O.D., entitled "Considerations When Prescribing Large Degrees of Prism", which appeared in "Optical Journal and Review of Optometry", Jan. 1, 1965, describes the use of large degrees of prism in eyeglasses for correcting eye defects, particularly diplopia or double vision. Note in the second full paragraph of page 23, it is indicated that by properly choosing the large prism factor, the prism in combination with the patient's remaining muscle function will correct the double vision problem. It is noted that vertical correction of double vision problems is most difficult insofar as attaining the combination of both prism and muscle correction. The prism factor is apparently chosen by having a patient's head fixed in position, and requesting the patient to gaze at an object with both eyes open, while different lenses are tested, until a prism factor is found for correcting the double vision problem. As a result only a single rigid line of vision with complete correction of diplopia is obtained.

SUMMARY OF THE INVENTION

An object of the invention is to provide an improved method and apparatus for correcting either one of vertical and lateral double vision problems.

Another object of the invention is to provide a method and apparatus for determining an extended prism factor for use in eyeglasses for correction of either one of vertical and lateral double vision problems, wherein the prism factor chosen is selected at a time of muscle relaxation of the affected eye, for thereby permitting greater involvement of the eye muscles in combination with the prism for extending the correction of the double vision problem over a much greater range of vision or angular movement of the head away from the original line of correction.

Yet another object of the invention is to provide a method and apparatus for substantially correcting either one of vertical and lateral double vision problems over the range of vision required for normal activities of a user of associated eyeglasses.

With the problems of the prior art in mind, these and other objects of the invention are provided by a method and apparatus for prescribing a prism factor to eyeglasses for correcting vertical and/or lateral double vision problems, wherein the method includes the steps of retaining a patient's head in a substantially fixed position, while having the patient gaze at an image, preferably located a distance in front of him/her, with the normal eye being open for establishing the gaze, and the defective eye being closed. After a period of time sufficient for the muscles of the defective eye to relax, the patient is asked to continue to gaze at the target object with his/her good eye, and open his/her defective eye, and immediately report upon where the double image first occurs upon opening the defective eye relative to a measurement grid located behind the target object. The measurement is made before the muscles of the defective eye have an opportunity to operate to extend or contract for merging the double image to the extent possible with the image being observed by the other eye. The correct extended prism factor is obtained when immediately upon opening the defective eye when wearing the corrective eyeglasses, the patient observes a normal image without any double image or double vision problems. In this manner, the patient's range of vision away from the rigid line of double vision correction is extended to the maximum extent possible for obtaining a substantially normal range of vision for everyday activities, by permitting the muscles of the eye to act in combination with the corrective prism for providing correction to the greatest extent possible.

Another embodiment of the invention provides a narrow elongated measuring grid mounted upon a tripod for orienting the measurement grid in a horizontal or vertical plane at a distance from the patient.

In yet another embodiment, the measurement grid includes a plurality of colored lights, for example, equally spaced a predetermined measured distance from one another along the grid, with the centralmost colored light serving as the target object for a patient to gaze at with his/her good eye for carrying out the method of the invention. When the patient opens his/her defective eye, he/she will report upon where the double image occurs relative to two successive colored lights immediately upon opening his/her eye for permitting easy measurement of the maximum distance of the double image.

In another embodiment of the invention, the measurement grid is provided by projecting the grid from a colored slide upon a screen located a predetermined distance from a patient.

BRIEF DESCRIPTION OF THE DRAWINGS

Various embodiments of the present invention are described and illustrated below with reference to the drawings, in which like items, are identified by the same reference designation, wherein.

DETAILED DESCRIPTION OF THE INVENTION

Figure 1:
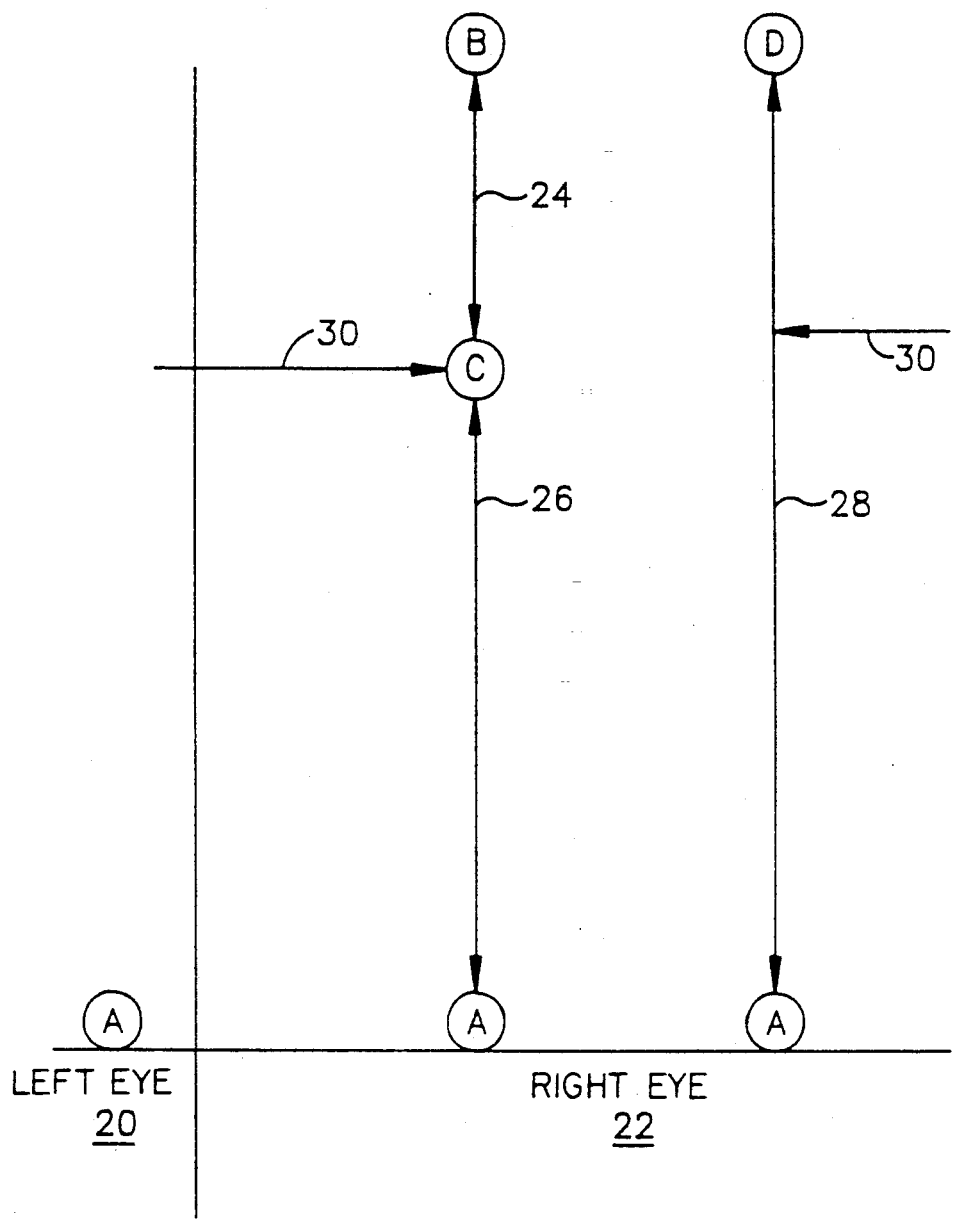
FIG. 1 is a chart illustrating a comparison of a prior method of establishing a prism factor for correcting double vision problems, directly compared to the method of the present invention.

The present inventor was left with a vertical double vision problem in his right eye, subsequent to a retina operation performed on this eye. A number of years later, a cataract operation was performed on his left eye. Subsequent to this, an ophthalmologist prescribed new eyeglasses, and made an effort to correct the inventor's double vision problem by including certain degrees of prisms in the lenses. The prism factors were established by the ophthalmologist, by having the inventor gaze at an object with both eyes open while retaining his head in a relatively fixed position, whereupon different prism factors were substituted in test lenses positioned before the inventor's right eye, until the double vision did not appear. The inventor obtained considerable relief using the new glasses, but found that his vision was limited to a more or less single angle of vision (the rigid line of double vision correction established by the ophthalmologist in prescribing the prism factor) at which the double vision did not appear. Unfortunately, the present inventor found that any deviation from this line of vision resulted in the reappearance of the double vision problem in varying degrees.

The present inventor worked diligently to develop a method for substantially eliminating his double vision problem. Eventually he developed a method for extending the prism factor in the eyeglass lenses, in order to permit the eye muscles of his right eye, in this example, to have a greater range of action in participating in combination with the corrective prism for correcting the double vision problem.

With regard to the inventor's double vision problem, the images of his left and right eyes are vertically apart. In this example, the natural reaction of the inventor's faulty right eye is to merge its image with that of his left eye, by his brain ordering the muscles of the right eye to stretch or extend so that the images of the two eyes merge to the greatest extent possible. The present inventor observed that if he closed his defective right eye for a sufficient time to permit the muscles thereof to relax, while keeping his head still and gazing at an object at a distance with his left eye, that immediately upon opening his right eye, for a seemingly fraction of a second the image observed by the right eye appears at a higher level than that of the left eye, and substantially immediately begins moving toward the left eye image because of the action of the eye muscles. Unfortunately, because of the defective condition of his right eye, the image relative to the right eye moves only a portion of the distance initially between the images of the right and left eyes, because of the limitation of correction available from movement of the muscles of the right eye.

At this point, the inventor recognized that with both eyes open, the eye muscles of his right eye are in a continuous state of extreme extension, preventing any further corrective action by the muscles of the right eye. He further recognized that it is at this point that his ophthalmologist attempted to close the gap or remaining distance between the right eye image and the left eye image by adding prisms to the eyeglass lenses being prescribed, for making the necessary correction for causing the two images to merge. The inventor further recognized that this combined action of the eye muscles and the prisms resulted in a single, rigid corrected line of vision. Any deviation the inventor made from this line of vision resulted in the reappearance of the double vision problem in varying degrees, unless the inventor purposely moved his head while maintaining his eyes for gazing along the single rigid line of correction. After much study and analysis, the inventor recognized, as indicated above, that the muscles of his right eye, as corrected by then known methods, are already in a fully extended position, providing no further assistance for aligning the images of the right and left eyes. Only very minor deviations from the rigid line of sight could possibly be masked by the dominance of one eye over the other.

The original prescription prescribed by the inventor's ophthalmologist, determined with then known methods, called for a prism diopter of nine. The inventor next embarked upon conducting experiments for proving the method that he developed, as shown in FIG. 1 in diagrammatic form, for substantially improving the correction of his vertical double vision problem, in this example. As shown by the chart in FIG. 1, vertical section 20 is associated with left eye vision, whereas vertical section 22 is associated with right eye vision. The reference designation "A" is indicative of the image level of the normal left eye, in this example, when gazing at a target object. Reference designation "B" is the image level of the defective right eye immediately after opening, relative to the image level at "A" of the normal left eye. Reference designation "C" shows the image level of the right eye after remaining open, and after the eye muscles thereof have attempted to merge the right eye image with the left eye image. The distance designated by arrow 24 between levels "B" and "C" is the extent of muscle correction available in the defective right eye, in this example. The distance between level "C" and level "A" is designated by the arrow 26, and is the distance a prism of a diopter value required to obtain correction along a rigid line of sight if selected via the prior method for merging the right eye image with the left eye image. Reference designation "D" is at the same level as image level "B", but is associated with distance arrow 28, for showing the substantial total correction of the double vision problem achieved by the embodiment of the invention for increasing the prism factor, relative to the prior method, to merge the right eye image immediately upon opening the right eye, with substantially no associated muscle involvement, with the level "A" of the normal left eye image. The arrows 30, are indicative of the rigid line of vision correction obtained by the prior method for combining the action of prisms and the muscles of the affected eye for causing the image of the defective eye to move the distance 26 via the addition of the prism factor to the eyeglasses, with the muscles being fully extended for providing correction to the extent of distance 24, in this example. In both the prior and present methods, the selection of a prism factor or strength of the prism is directly related to the extent of correction required to overcome the eye defect, i.e. to the magnitude of the defect in the eye being corrected.

Figure 2:
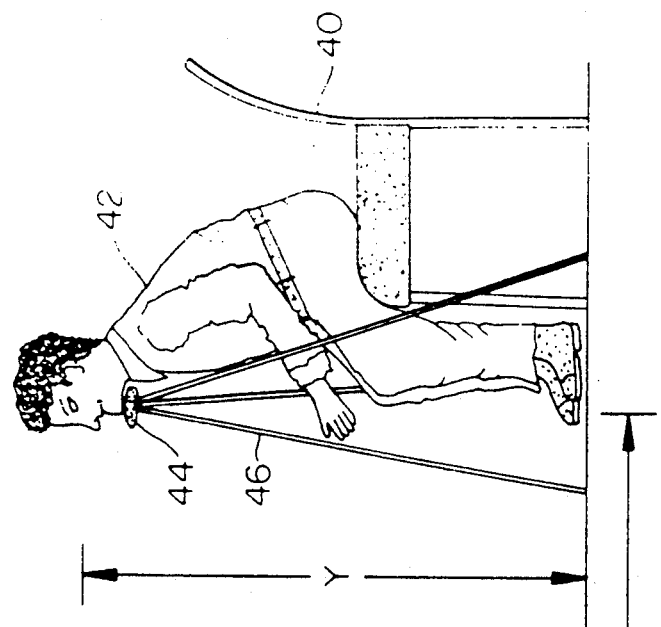
FIG. 2 is a pictorial view showing apparatus for one embodiment of the invention in correcting vertical double vision.
Figure 2:
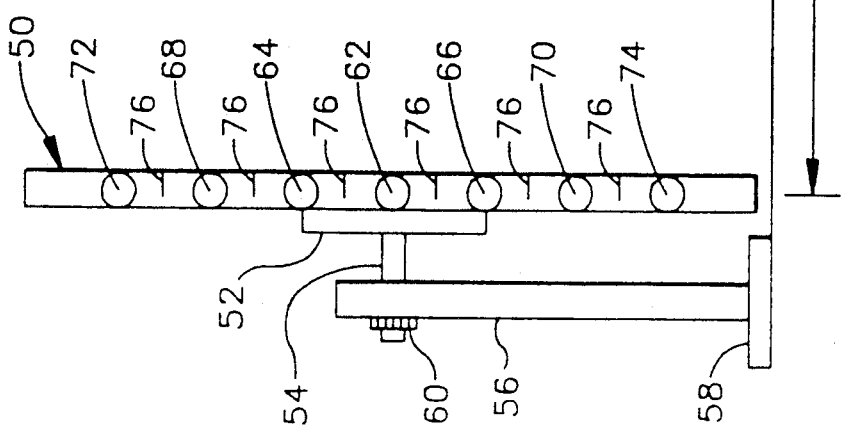
Figure 3:
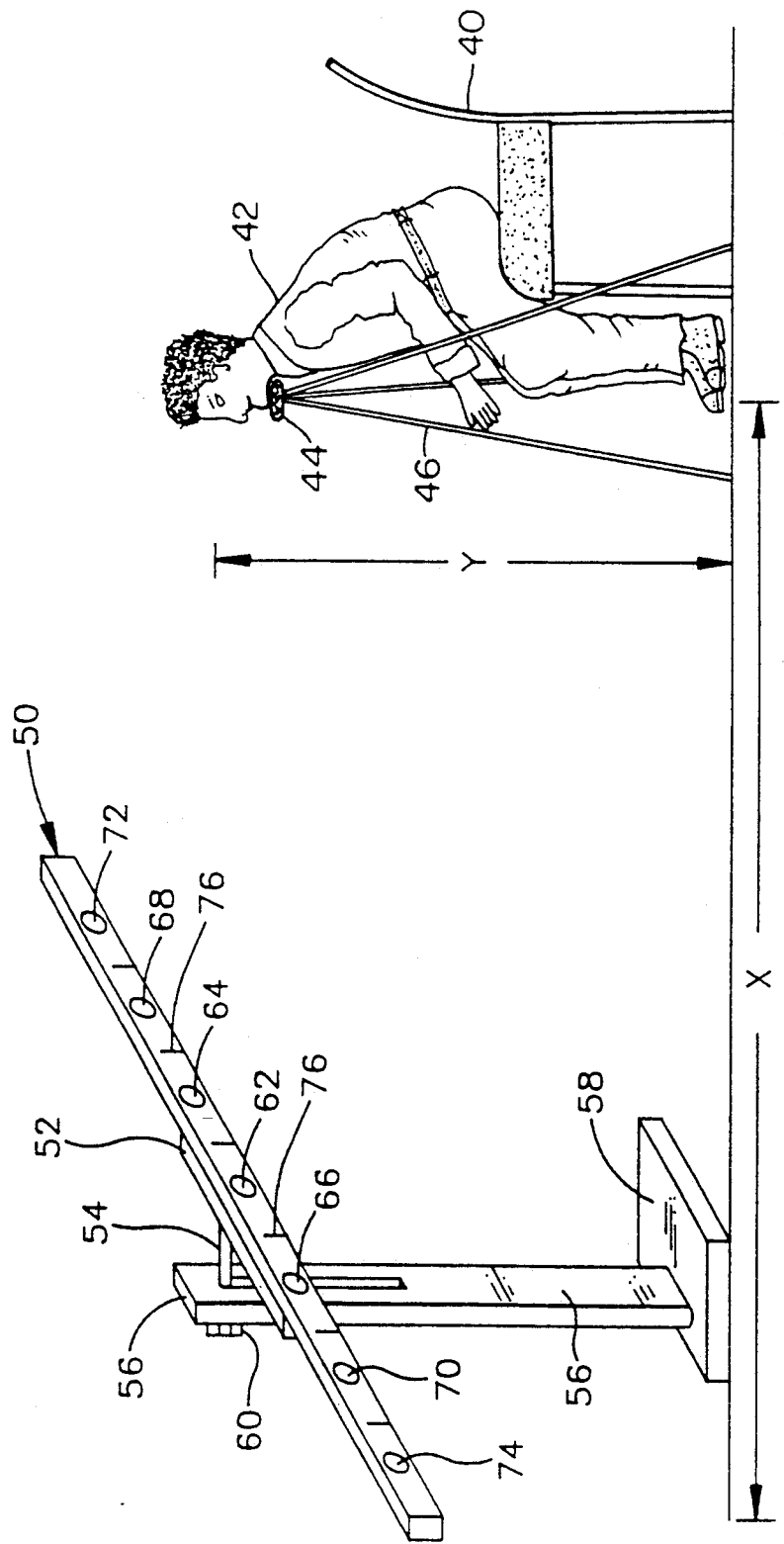
FIG. 3 shows apparatus for another embodiment of the invention, for establishing a prism factor for correcting lateral double vision problems.

In another embodiment of the invention, the present inventor conceived the apparatus shown in FIGS. 2 and 3, for facilitating the prescription of extended diopter prisms in eyeglasses for correcting vertical and lateral double vision problems, respectively. The apparatus includes a chair 40 for a patient 42 to comfortably sit upon, and face other portions of the apparatus. In this example, a head or chin support 44 is mounted upon an ordinary camera tripod 46. Through experimentation, it was determined that in the preferred embodiment, the height of the chair is adjusted to maintain the eye level "Y" of the patient 42 while sitting at a height to maintain the eye level at about four feet from the floor 48. The height of tripod 46 is adjusted for permitting the patient 42 to lean slightly forward and rest his/her chin on the chin support 44, with his/her eye level being maintained at the preferred height. This provides for the patient to gaze slightly downward at a target image.

A rectangular measuring column or grid 50 is rigidly mounted at a central rear portion to a rotatable arm 52. The rotatable arm 52 is connected via a rod 54 threadably retained through an upper portion of a vertical support member 56, the lower end of the latter being secured to a base member 58. A knurled locking ring 60 threadably mounted upon the end of the rod 54 protruding from the support member 56, permits measuring column 50 to be rotated and locked into a vertical position as shown in FIG. 2, with the knurled ring or knob 50 being rotated for securing the rod 54 and measuring column 50 in position. The knurled knob 60 is loosened for permitting the measuring column 50 to be rotated to a horizontal position as shown in FIG. 3, and thereafter the knob 60 is rotated for locking rod 54 and its associated measuring column 50 in place. In this manner, the measuring column 50 can readily be used for prescribing extended prism factors for correcting either vertical double vision, or lateral double vision problems, as will be described below.

In an engineering prototype for the apparatus, the measuring column 50 is about one inch by two inches at its ends, and about 84 inches long. In this example, a white colored light, serving as a target object 62, is placed at the approximate center of measuring column 50. Red colored light sources or light bulbs 64 and 66 are mounted on either side of and at a distance of about 12 inches from the white light source 62, in this example. Also, blue light sources 68 and 70 are rigidly mounted about 12 inches from the red light sources or light bulbs 64 and 66, respectively, towards the ends of measuring column 50. Another red light source or light bulb 72 is rigidly mounted on column 50, 12 inches from blue light source 68, toward the associated end of column 50. Still another red light source 74 is rigidly connected to column 50, 12 inches from blue light source 70, toward the associated closest end of column 50, as shown. It should be noted that the dimensions of the prototype apparatus, and the coloring of the light sources or light bulbs 62, 64, 66, 68, 70, 72, and 74, are not meant to be limiting, and may be different than herein indicated. For example, green colored lights can be used for light sources 72 and 74. The aforesaid light sources can also be provided in a conventional manner via battery power, or an AC supply. Note that the column 50 may also include a grid of measurement lines 76 spaced equidistant from one another and associated ones of the light sources, as shown. Further note that the pictorial drawings of FIGS. 2 and 3 are not necessarily to scale, or in proper perspective, and are meant for purposes of illustration only. For example, the scale for eye level "Y" is greater than the scale for measuring column 50, as drawn, for giving emphasis to the various features of the invention.

The present inventor conceived the measuring 50 to provide a measurement grid that would have measuring points that are readily observable and identifiable by a patient. However, the measurement grid can be provided in a number of alternative ways. For example, a slide projector can be used to project a measurement grid from a colored slide onto a screen or wall an appropriate distance from a patient being tested, with the grid being also projected at a desired level from the floor. In this regard, the present inventor developed a measurement grid on a colored slide, and a means for rotating the slide when in a slide projector, for holding the slide at a predetermined angle, for projecting the measurement grid on a screen or wall at any desired angle. Also, a number of different colored slides may be prepared for using an unmodified slide projector to project a measurement grid at any desired angle.

Through experimentation, in using the apparatus shown in FIGS. 2 and 3, the present inventor determined that by adjusting the measuring column 50 to provide for the target image 62 to be about 12 inches lower than the eye level of the patient being tested, approximates to a substantial degree the angle of vision encountered in a person's normal life activities. The present inventor recognized that a downward angle of vision is used almost exclusively in such activities as reading, eating, watching television, driving a car, and other such activities. He further recognized that most people walk through their homes or offices, for example, fully conscious of the floor, the furniture, the pictures on the wall, and so forth, but hardly noticing the ceiling.

Experiments conducted by the present inventor using the apparatus of FIGS. 2 and 3 will now be described in detail.

Note that whenever reference is made to the defective eye image with that eye closed, the image referred to is the one appearing immediately upon a patient's opening his/her eye, before muscle action of the patient has changed the configuration of the associated eye to move the image to a different level.

A patient 42 is seated on a chair 40, with his/her chin positioned on chin rest 44, as shown. As previously mentioned, the measuring column 50 is adjusted for retaining the target image 62 at a level about twelve inches below the horizontal plane of a patient 42 positioned as shown. As previously mentioned, in cases where vertical diplopia is to be corrected, the measuring column 50 is vertically positioned as shown in FIG. 2, whereas for correcting horizontal diplopia, the measuring column 50 is positioned as shown in FIG. 3. The procedure for testing a patient to prescribe an appropriate prism factor is substantially the same whether correcting for vertical or horizontal diplopia. The patient 42 is requested to hold their head still with their chin on the chin rest 44, as previously mentioned. He/she is then requested to fix their gaze on the target image 62, in this example a white light source, and to thereafter close their affected eye or the eye to be corrected. After a period of time sufficient for the eye muscles of the affected eye to relax, the patient 42 is requested to open the affected eye, and immediately report upon such eye opening where the double image initially appears on the measurement grid relative to the various colored lights and intermediate measurement lines 76, as previously described. This test can be repeated a number of times to ensure correctness of the measurement. From this information, the physician or technician would then select an appropriate prism factor depending upon the maximum measurement of the double image from the target image 62. The selected lens is then positioned before the patient's affected eye, using conventional eyeglass test holders or eyeglass test equipment, and the procedure is repeated. The patient 42 is asked to continue to gaze with his/her other eye at the target image 62, and to close the affected eye. After a period of time, he/she is asked to open the affected eye and immediately report upon whether the selected eyeglass lens under test provided for complete merging of the images of each eye upon opening the affected eye, or whether a double image is still observed and where on the measurement grid of the measuring column 50 the double image still appears. If a double image still appears, the physician or technician would then select a higher prism factor. Upon obtaining a prism factor for providing complete merger of the right and left eye images upon a patient 42 opening his/her affected eye, as previously described, the patient 42 is asked to continue to hold his/her head steady, and to move his/her eyes up and down relative to the target image 62, to determine whether any double images are observed. If any double images are observed, the patient 42 is asked to report where these images occur relative to the measurement grid, to permit the physician to determine the range of fusion or merger obtained with the prism factor selected. The preferred prism factor is the minimum necessary for providing complete merger of the images observed by both eyes, and movement of the eyes to the upwardmost and downwardmost extremes relative to the target image 62 for correction of vertical diplopia, or to the rightmost and leftmost extremes relative to the target image 62 in correcting for horizontal diplopia.

In conducting experiments to correct the vertical diplopia of his right eye, the present inventor first noted that the eyeglass prescription provided by his ophthalmologist called for a prism diopter of 9, as determined by conventional and known procedures described above. He conducted his tests or experiments with the measuring column 50 positioned in the vertical plane as shown in FIG. 2, as previously described for correcting vertical diplopia. The present inventor determined that without use of any corrective glasses, the images of his left and right eyes were 24 inches apart. He next determined that when wearing eyeglasses with a prism of 9 diopters, as previously described, upon opening his right eye when gazing at the reference or target light or image 62 with his other eye, then immediately upon opening the right eye a double image occurred about 6 inches from the target image 62, which image then moved to within two inches of the target image through muscle action of the right eye. He found that in order to achieve perfect merger of the images, he had to tilt his head backward. He also observed that when looking around a room, there was a constant realization of double vision. Also, when wearing the prescribed glasses, he found that when driving or riding in an automobile, he had to tilt his head backward in order to align the lines of the highway, and that such alignment only occurred at certain distances.

When wearing eyeglasses with a prism of 11 diopters for the right eye, the present inventor determined that upon opening his right eye, the double image was initially four inches from the target image being observed by his other eye, which distance closed to within one inch via subsequent muscle action of the right eye. He further determined that it was possible in this case to achieve almost complete merger of the images when he moved his eyes downward below the established target image 62 to observe the red light source 66 and blue light source 70, but that double images occurred when he moved his eyes upward to observe the red light sources 64 and 72 and blue light source 68, unless he tilted his head backward, whereupon merger was obtained for the images.

The inventor repeated the test for glasses including a prism of 13 diopters for the right eye. He determined that such a prism factor provided substantially complete merger of the images of the right and left eyes immediately from the time of opening his right eye. Such substantial merger of the images occurred when he moved his eyes to observe the light sources 66, 70 and 74 below the target light source 62, and the light sources 64 and 68 above the target light source 62. However, he did observe that when moving his eyes to gaze at the light source 72, located in the test performed at about 6 feet from the floor, that he required a slight backward movement of his head in order to obtain merger of the images of his right and left eyes. He repeated the test wearing eyeglasses having a prism factor of 15 diopters for the right eye, and determined that very little additional improvement was obtained relative to the 13 diopter prism. He further determined that after wearing eyeglasses having a 15 diopter prism, that he experienced a degree of eye strain, which he did not experience when wearing eyeglasses with a 13 diopter prism.

The eyeglasses with 11, 13, and 15 diopter prism factors for the right eye all use single distance lenses. The present inventor also obtained two pairs of reading glasses with 13 diopter and 15 diopter prisms for the right eye, and determined that the 15 diopter lenses continued to cause eye strain, whereas the 13 diopter lenses provided substantially complete correction of his vertical diplopia problem. As a result, the eyeglasses with a 13 diopter prism for the right eye were adopted for use for both reading glasses, and in distance eyeglasses.

After more than six months of using the eyeglasses with a number 13 diopter prism for correcting the vertical diplopia of his right eye, the present inventor determined that his vertical diplopia problem is substantially corrected. He only observes a minor degree of vertical diplopia when he forces his eyes to move to extreme angles of vertical vision from a normal plane of vision while holding his head still for comfortably gazing out at the normal plane of vision. Through use of the prism factor established by his method, the present inventor has further determined that when driving an automobile, or riding in an automobile, there is substantially no double image problem with highway lines, nor are image problems encountered when he looks around a room at pictures on a wall, for example. Previously, in using the eyeglasses with a prism factor of 9 diopters as previously prescribed through conventional techniques, he found that when wearing such eyeglasses, upon looking around a room for example, pictures on a wall tended to bob up and down.

As previously mentioned, the present method permits the determination of a prism factor for eyeglasses for correcting either horizontal or vertical diplopia in a manner allowing the eye muscles their full range of flexibility, for significantly enhancing the range of total correction of the diplopia problem. The present method overcomes the limitations of the prior testing method that is restricted through use of a single, rigid line of correction that diminishes the ability of the eye muscles to be involved in the corrective process over a range of eye movement.

The present method is not limited in cases where patients have experienced diminished capacity of their eye muscles due to partial or total paralysis caused by a stroke or other brain damage. On the contrary, the present method substantially depends upon a patient having at least a partial functional ability of their eye muscles, the greater the available function, the greater the degree of correction that can be provided through use of the present method. As described, the present method is directed towards providing a wider range of correction of certain cases of vertical or horizontal (lateral) diplopia, by permitting determination of a prism factor large enough for merging double images observed by a patient at the widest point of divergence, thereby reserving substantially the full range of muscle power or correction available in a patient's affected eye for providing a greater range of vertical or lateral diplopia correction.

Although various embodiments of the present method are shown and described herein, they are not meant to be limiting. Those of skill in the art may recognize certain modifications to these various embodiments of the invention, which modifications are meant to be covered by the spirit and scope of the appended claims.

What is claimed is:

1. A method for prescribing a prism factor for eyeglasses for substantially correcting double vision problems, in a manner substantially maximizing the involvement of the eye muscles in combination with the prism to substantially extend the range of correction, the method comprising the steps of:
    (A) establishing a target image;
    (B) establishing a measurement grid on each side of said target image;
    (C) positioning a patient a predetermined distance from the target image;
    (D) retaining a patient's head in substantially a fixed position for gazing out at said target image along a predetermined line of sight;
    (E) requesting said patient to close their defective eye, while keeping their other eye open and gazing at said target image;
    (F) requesting said patient after a period of time to open their defective eye and immediately indicate where a double image of said target image occurs on said measurement grid, for obtaining the substantial maximum distance of the double image from said target image; and
    (G) selecting a prism factor for an eyeglass lens for substantially reducing the measured distance of said double image from said target upon said patient opening their defective eye.

2. The method of claim 1 further including the steps of:
    (H) fitting said patient with test eyeglasses incorporating a lens with the selected prism factor for the defective eye;
    (I) repeating steps (A) through (F) to test the correction obtained with the first selected prism factor;
    (J) request said patient while still retaining their head in position, to move their eyes along the measurement grid to the extreme possible on either side of said target image;
    (K) selectively slightly increasing the prism factor relative to the first selected prism factor if a double image still occurs, and repeating steps (H) and (J) until a prism factor is determined that eliminates the double image in step (J) to the greatest extent, whereby the latter prism factor is prescribed; and
    (L) selecting a slightly decreasing prism factor in steps relative to the first selected prism factor if a double image does not occur in the first performance of steps (H) and (J), for obtaining for prescription the substantially lowest prism factor found to eliminate a double image in performing steps (H) and (J).

3. The method of claim 1, where step (A) further includes the steps of:
    mounting a first source of light, for serving as said target image, on an elongated column;
    adjusting the height of said column for placing said first source of light at a comfortable height relative to the centralized line of sight of said patient; and
    applying power to said first source of light for making it easily seen or observed by said patient.

4. The method of claim 3, further including the steps of:
    mounting a plurality of second and third sources of light on either side of said first source of light, respectively, the latter being located in the approximate center of said column; and
    spacing said first source of light, and said plurality of second and third sources of light to be equidistant by a predetermined measure from one another in juxtaposition, respectively, for providing a portion of said measurement grid.

5. The method of claim 4, further including the steps of:
    making said first source of light a color different from that of any of said plurality of second and third sources of light; and
    selecting other colors for said plurality of second and third sources of light.

6. The method of claim 4, further including the step of:
   securing said column in a vertical plane for establishing a prism factor for patients having a vertical double vision problem.

7. The method of claim 4, further including the steps of:
   securing said column in a horizontal plane for establishing a prism factor for patients having a lateral double vision problem.

8. The method of claim 1, wherein step (C) further includes the step of having said patient sit on a chair.

9. The method of claim 8, wherein step (D) further includes the step of positioning a chin rest at a comfortable height for the patient to place their chin upon for retaining their head still while gazing at said target image.

10. The method of claim 9, wherein said patient is positioned about 12 feet from said target image.

11. The method of claim 4, further including the step of:
   selecting different colors for said first through N sources of light.

12. The method of claim 5, wherein said step of selecting other colors for said plurality of second and third sources of light, further includes selecting the same color for every pair of said second and third sources of light located equidistant on either side of said first source of light, respectively.

13. The method of claim 4, further including the step of placing readily observable equidistant measurement markings on said column between juxtaposed ones of said first source of light, and said second and third pluralities of sources of light, respectively.

14. An apparatus for use in carrying out a method for prescribing a prism factor for eyeglasses, for substantially correcting vertical or lateral double vision problems in a manner substantially maximizing the involvement of a patient's affected eye muscle in combination with a lens incorporating said established prism factor, comprising:
   a measurement grid including
   an elongated straight light column;
   a plurality of equidistantly spaced sources rigidly mounted upon said light column, a centrally located one of said light sources serving as a target image, said plurality of light sources serving to provide a portion of measurement marks or indicators for said measurement grid; and
   means for selectively retaining said elongated light column in a desired orientation relative to a patient, one orientation being vertical relative to vertical double vision problems, another orientation being horizontal relative to horizontal double vision problems;
   a chin rest;
   support means for retaining said chin rest at a height permitting a patient seated upon a chair to comfortably hold their chin on said chin rest, while being positioned for holding their head still in gazing out along a line of sight at said light-source representing said target image, said measurement procedure involving asking said patient to close their defective eye to be corrected, while continuing to gaze with their other eye at said target image, and after a period of time opening their defective eye and reporting immediately as to the location on the measurement grid where the double image initially appears relative to given ones of said plurality of light sources, for providing a measurement permitting prescription of a prism factor for a corrective lens for the defective eye that maximizes eye muscle involvement in combination with the prescribed lens for providing correction of the double vision over a maximum range of angles away from the rigid line of correction for establishing the prism factor.

15. A method for prescribing a prism factor for eyeglasses for substantially correcting double vision problems, in a manner substantially maximizing the involvement of the eye muscles in combination with the prism to substantially extend the range of correction, the method comprising the steps of:
   (A) establishing a target image;
   (B) establishing a measurement grid on each side of said target image;
   (C) positioning a patient a predetermined distance from the target image;
   (D) retaining a patient's head in substantially a fixed position for gazing out at said target image along a predetermined line of sight;
   (E) requesting said patient to close their defective eye, while keeping their other eye open and gazing at said target image;
   (F) requesting said patient after a period of time to open their defective eye and immediately indicate where a double image of said target image occurs on said measurement grid, for obtaining the substantial maximum distance of the double image from said target image;
   (G) selecting a prism factor for an eyeglass lens for reducing the measured distance of said double image from said target image upon said patient opening their defective eye;
   (H) fitting said patient with test eyeglasses incorporating a lens with the selected prism factor for the defective eye;
   (I) repeating steps (A) through (F) to test the correction obtained with the first selected prism factor;
   (J) request said patient while still retaining their head in position, to move their eyes along the measurement grid to the extreme possible on either side of said target image; and
   (K) selectively slightly increasing prism factor relative to the first selected prism factor if a double image still occurs, and repeating steps (H) and (J) until a prism factor is determined that eliminates the double image in step (J) to the greatest extent, whereby the latter prism factor is prescribed.

* * * * *

UNITED STATES PATENT AND TRADEMARK OFFICE
CERTIFICATE OF CORRECTION

PATENT NO. : 5,302,981
DATED : April 12, 1994
INVENTOR(S) : Paul C. Wirtz

It is certified that error appears in the above-indentified patent and that said Letters Patent is hereby corrected as shown below:

Column 6, line 28 after "measuring" insert --column--.

Column 11:
Claim 11, line 3 change "N" to --third--.

Column 11, line 44, after"spaced", insert --light--.

Signed and Sealed this

Second Day of August, 1994

Attest:

BRUCE LEHMAN

*Attesting Officer*  *Commissioner of Patents and Trademarks*